United States Patent
Schweiger et al.

(10) Patent No.: US 6,342,458 B1
(45) Date of Patent: Jan. 29, 2002

(54) LITHIUM DISILICATE GLASS CERAMICS DENTAL PRODUCT

(75) Inventors: Marcel Schweiger, Chur (CH); Martin Frank, Schaan (LI); Volker Rheinberger, Vaduz (LI); Wolfram Hoeland, Schaan (LI)

(73) Assignee: Ivoclar AG (LI)

( * ) Notice: Subject to any disclaimer, the term of this patent is extended or adjusted under 35 U.S.C. 154(b) by 0 days.

(21) Appl. No.: 09/379,450

(22) Filed: Aug. 23, 1999

Related U.S. Application Data (62) Division of application No. 08/924,232, filed on Sep. 5, 1997, now Pat. No. 5,968,856.
(60) Provisional application No. 60/040,827, filed on Mar. 20, 1997.

(30) Foreign Application Priority Data

Sep. 5, 1996 (DE) .......................... 196 35 940
Nov. 6, 1996 (DE) .......................... 196 47 739

(51) Int. Cl.[7] .................. C03B 27/012; C03B 32/00; A06K 6/02
(52) U.S. Cl. .................. 501/5; 106/35; 501/63; 501/64; 501/68; 501/69; 433/218; 433/215; 433/202.1; 433/212.1
(58) Field of Search ................ 106/35; 501/5, 501/63, 64, 68, 69; 433/218, 215, 212.1, 202.1

(56) References Cited

U.S. PATENT DOCUMENTS

| | | | |
|---|---|---|---|
| 3,812,689 A | 5/1974 | Reade | 65/33 |
| 4,189,325 A | 2/1980 | Barrett et al. | 106/35 |
| 4,515,634 A | 5/1985 | Wu et al. | 106/35 |
| 5,039,631 A | 8/1991 | Krashkevich et al. | 501/69 |
| 5,122,671 A | 6/1992 | Buchanan et al. | 501/69 |
| 5,580,363 A | 12/1996 | Goto et al. | 65/29.18 |
| 5,618,763 A | 4/1997 | Frank et al. | 501/5 |
| 5,756,409 A | 5/1998 | Van Dijen et al. | 501/89 |

FOREIGN PATENT DOCUMENTS

| | | |
|---|---|---|
| EP | 0 690 031 A1 | 1/1996 |
| GB | 1 424 398 | 2/1976 |
| JP | 55-126546 | 9/1980 |
| JP | 07-250848 | 10/1995 |
| JP | 08-040744 | 2/1996 |

*Primary Examiner*—C. Melissa Koslow
(74) *Attorney, Agent, or Firm*—Nixon Peabody LLP (57) ABSTRACT

High-strength sinterable lithium disilicate glass ceramics are described which can be further processed in particular by pressing in the viscous state to shaped dental products.

10 Claims, 3 Drawing Sheets

LITHIUM DISILICATE GLASS CERAMICS DENTAL PRODUCT

This is a divisional of U.S. patent application Ser. No. 08/924,232 filed Sep. 5, 1997, now U.S. Pat. No. 5,968,856, which claims the benefit of U.S. Provisional Patent Application Serial No. 60/040,827, filed Mar. 20, 1997.

FIELD OF THE INVENTION

The invention relates to sinterable lithium disilicate glass ceramics and in particular those which, by virtue of their properties, are suitable for the production of shaped dental products by plastic deformation with the action of pressure and heat.

BACKGROUND OF THE INVENTION

Lithium disilicate glass ceramics are known. EP-B-536 479 describes self-glazed lithium disilicate glass ceramic articles which are not, however, intended for dental applications. The glass ceramics are free of $La_2O_3$ and are formed in the usual manner by melting suitable starting materials, pouring the melt into molds to produce articles, and subsequently heat treating the articles.

Lithium silicate glass ceramics are also disclosed in EP-B-536 572. They are given structure and color by the dispersion of a finely divided colored glass onto their surface, and they are used as lining units for building purposes. They are manufactured in a conventional manner in that suitable starting materials are melted, the melt is molded to a desired body, and the body is heat-treated together with dispersed colored glass. $La_2O_3$ is not, however, contained in the glass ceramic.

Glass ceramics based on $SiO_2$ and $Li_2O$ which contain large quantities of poisonous arsenic oxide are known from DE-C-1 421 886.

Moreover, the use of lithium disilicate glass ceramics in dental technology is also known, but these glass ceramics do not contain $La_2O_3$ or MgO. Further, only conventional methods are used to process these glass ceramics to dental products, where a heat treatment is carried out to precipitate crystals only on homogeneous bodies, namely monoliths formed from a glass melt, such as small glass block or slabs. Conventional methods of this kind, however, only allow volume crystallization to take place, not surface crystallization.

Examples of such glass ceramics and conventional methods for the production thereof are described in following documents.

A lithium disilicate glass ceramic with high strength suitable for the preparation of dental crowns and bridges is described in U.S. Pat. No. 4,515,634.

A high-strength lithium disilicate glass ceramic is also described in U.S. Pat. No. 4,189,325 wherein said glass ceramic necessarily contains CaO to improve the flow and also platinum and niobium oxide to produce very fine and uniform crystals.

Glass ceramics containing lithium oxide and silicon oxide for the preparation of dental prostheses, which contain very large quantities of MgO, are described in FR-A-2 655 264.

Finally, U.S. Pat. No. 5,507,981 and WO-A-95/32678 describe lithium disilicate glass ceramics which may be further processed to formed dental products by special methods, wherein pressing in the viscous, flowable state at elevated temperatures to the desired dental product takes place. No further details are given regarding the production of the slabs or buttons used during this process. A conventional method is also used to produce the glass ceramic, in that homogeneous glass bodies, such as slabs, for example, are heat-treated. A disadvantage of these methods is that they are very labor intensive for a dental technician, due to the use of a special heat-pressure deformable crucible. Moreover, the glass ceramic materials are heated to such an extent that crystals are no longer present in the molten material since the viscosity would otherwise be to high for pressing to the desired dental product. Consequently, the product processed is glass, not a glass ceramic.

The above-noted lithium disilicate glass ceramics have shortcomings, particularly when they are to be processed further in the plastic state to form a shaped dental product. Their viscosity is not ideally adjusted for such processing, so a controlled flow is not possible and the reaction with the investment material is undesirably high. Moreover, conventional glass ceramics have only poor dimensional stability on heating, so that dental restorations produced from them may be provided with a sintered-on glass or glass ceramic layer only with deformation. Finally, conventional lithium disilicate glass ceramics also frequently lack the necessary chemical stability for use as dental material, which is permanently being flushed with fluids of various kinds in the oral cavity.

SUMMARY OF THE INVENTION

The object of the invention is, therefore, to provide a lithium disilicate glass ceramic which exhibits optimum flow properties, and, at the same time, little reaction with the investment material when pressed in the plastic state to dental products. Further, the glass ceramic has high dimensional stability on heating, particularly in the range from 700° to 900° C., and has excellent chemical stability.

This object is achieved by the sinterable lithium disilicate glass ceramic of the present invention. The present invention also provides for a process of making the glass ceramic and dental products utilizing the glass ceramic.

DRAWINGS OF THE INVENTION

DETAILED DESCRIPTION OF THE INVENTION

The sinterable lithium disilicate glass ceramic according to the invention is characterized in that it includes the following components:

| Component | Wt. % |
|---|---|
| SiO$_2$ | 57.0 to 80.0 |
| Al$_2$O$_3$ | 0 to 5.0 |
| La$_2$O$_3$ | 0.1 to 6.0 |
| MgO | 0 to 5.0, particularly 0.1 to 5.0 |
| ZnO | 0 to 8.0 |
| K$_2$O | 0 to 13.5 |
| Li$_2$O | 11.0 to 19.0 |
| P$_2$O$_5$ | 0 to 11.0 |
| Color components | 0 to 8.0 |
| Additional components | 0 to 6.0 | wherein

| | | |
|---|---|---|
| (a) | Al$_2$O$_3$ + La$_2$O$_3$ | amount to 0.1 to 7.0 wt. % and |
| (b) | MgO + ZnO | amount to 0.1 to 9.0 wt. % |

Typically, the color components are formed from glass-coloring oxides (c) and/or coloring bodies (d) in the following quantities:

| | | |
|---|---|---|
| (c) | glass-coloring oxides | 0 to 5.0 wt. % and |
| (d) | coloring bodies | 0 to 5.0 wt. %. |

It is preferred that the glass ceramic essentially consists of the components mentioned above.

Lithium disilicate was detected by X-ray diffraction analyses as the main crystalline phase of the glass ceramic according to the invention.

There are preferred quantity ranges for the individual components of the lithium disilicate glass ceramic according to the invention. These may be chosen independently of one another and are as follows:

| Component | Wt. % |
|---|---|
| SiO$_2$ | 57.0 to 75.0 |
| Al$_2$O$_3$ | 0 to 2.5 |
| La$_2$O$_3$ | 0.1 to 4.0 |
| MgO | 0.1 to 4.0 |
| ZnO | 0 to 6.0, particularly 0.1 to 5.0 |
| K$_2$O | 0 to 9.0, particularly 0.5 to 7.0 |
| Li$_2$O | 13.0 to 19.0 |
| P$_2$O$_5$ | 0 to 8.0, particularly 0.5 to 8.0 |
| Color components | 0.05 to 6.0 |
| Additional components | 0 to 3.0 |

The glass ceramic according to the invention contains color components, namely glass-coloring oxides (c), coloring bodies (d), or mixtures thereof, in order to obtain a color match between a dental product produced from the glass ceramic and the natural dental material of the patient. The glass-coloring oxides, particularly TiO$_2$, CeO$_2$, Fe$_2$O$_3$ or mixtures thereof, serve only to obtain a shading, the main coloration being brought about by the coloring bodies. It is to be noted that TiO$_2$ does not act as a nucleating agent but, in combination with the other oxides, as a color component. The coloring bodies are metal oxides conventionally used in dental glass ceramics and, in particular, commercial isochromatic coloring bodies, such as doped spinels, doped ZrO$_2$, or mixtures thereof. The coloring bodies may be both non-fluorescing and fluorescing materials.

In addition to the components mentioned above, the lithium disilicate glass ceramic according to the invention may also contain additional components, for which B$_2$O$_3$, F, Na$_2$O, ZrO$_2$, BaO, SrO, or mixtures thereof, are particularly suitable. The viscosity of the residual glass phase of the glass ceramic may be influenced with B$_2$O$_3$ and F, and it is assumed that they shift the ratio of surface to volume crystallization in favour of surface crystallization.

To produce the glass ceramics according to the invention, the process described in more detail below for the production of dental products containing the glass ceramic is used in particular, wherein the forming of special shapes is not necessary.

The process according to the invention for the production of shaped dental products containing the sinterable lithium disilicate glass ceramic according to the invention is characterized in that (a) a starting glass which contains the desirable components discussed above is fused, (b) the glass melt is into glass granules, (c) the glass granules are comminuted to a powder, (d) Optionally, the coloring bodies are added to the powder, (e) the powder is compacted to a starting glass blank, and (f) the starting glass blank is subjected to a heat treatment.

In the process stage (a), a starting glass is melted, preferably at temperatures of 1200° to 1650° C. Suitable starting materials such as, for example, carbonates, oxides and fluorides, are mixed with one another and heated to the specified temperatures, resulting in the formation of the starting glass. If color-imparting oxides are to be used, these are added to the batch prior to melting. The addition of optionally present coloring bodies takes place in a later stage of the process, since their effect would be lost at the high temperatures prevailing in the glass melt.

The glass melt obtained is formed into glass granules. Preferably, the glass melt is then quenched in stage (b) by being poured into water and is thereby converted into glass granules. This procedure is usually also referred to as fritting.

The glass granules are then comminuted in stage (c) and in particular milled to the desired particle size with conventional mills. An preferred average particle size of the powder obtained is 1 to 100 μm, based on the number of particles, with 10 to 50 μm, being especially preferred.

Optionally, the addition of coloring bodies, if desired, then takes place in stage (d).

In stage (e), the powder is then compacted to a glass blank of the desired geometry and heterogeneous structure. This is carried out, in particular, at room temperature and pressures of, in particular, 500 to 2,000 bar are used. This process stage of pressing to a blank with a heterogeneous structure is important so that, in contrast to the procedures known from the prior art, surface crystallization takes place in addition to volume crystallization during the subsequent heat treatment in stage (f). Preferably, the heat treatment in stage (f) occurs under vacuum and in the temperature range from 400° to 1100° C. in order to achieve a dense sintering and to give a dental product in the form of a glass ceramic blank (also called an ingot or a pellet). Optionally, the heat treatment can occur in more than one step. The heterogeneous structure of the starting glass blank composed of starting glass powder particles pressed together allows controlled surface crystallization on the inner surface of the glass powder. This surface crystallization is identifiable by the fact that even without conventional volume nucleating agents, such as metals or $P_2O_5$, the heat treatment taking place in stage (f) leads to the formation of a lithium disilicate glass ceramic containing finely divided crystals. If $P_2O_5$ is used as a component of the starting glass, the heat treatment in stage (f) causes both surface crystallization and volume crystallization to take place. In conventional processes, on the other hand, blanks with a homogeneous structure are used, i.e. in which no particles of starting glass powder are present. The result of this is that surface crystallization is not possible.

The purpose of the heat treatment taking place in stage (f) is to initiate the crystallization of the starting glass blank and hence to form the glass ceramic which, after this process stage has ended, takes the form of a densely sintered glass ceramic blank. This glass ceramic blank usually has the shape of a small cylinder or a small slab.

A final dental product, such as a bridge, a crown, a partial crown, an inlay, an onlay, a post-construction, or a veneer, may be produced from the glass ceramic blank.

Two preferred options for producing the final dental product are the two options (g1) or (g2) given below.

On the one hand, in stage (g1), glass ceramic blank is subjected to plastic deformation, i.e. a heat treatment under pressure. As discussed in detail below, preferably, plastic deformation takes place at a temperature of 700° to 1200° C. and by the application of a pressure of 2 to 10 bar to form a dental product of the desired geometry. In this process, the blank in the plastic state is pressed into a die cavity conforming with the dental product of the desired shape. The pressing furnace used for this purpose is marketed as the Empress® furnace by Ivoclar AG, Liechtenstein.

Figure 1:
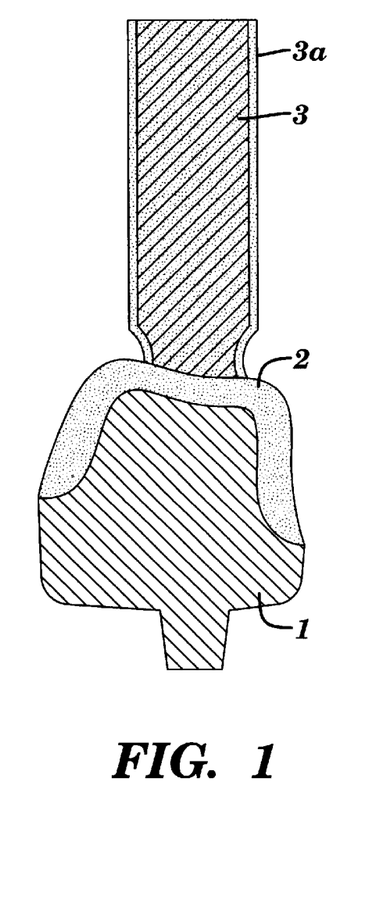
FIG. 1 shows a model with a form for a pouring channel produced on a working stump.
Figure 2:
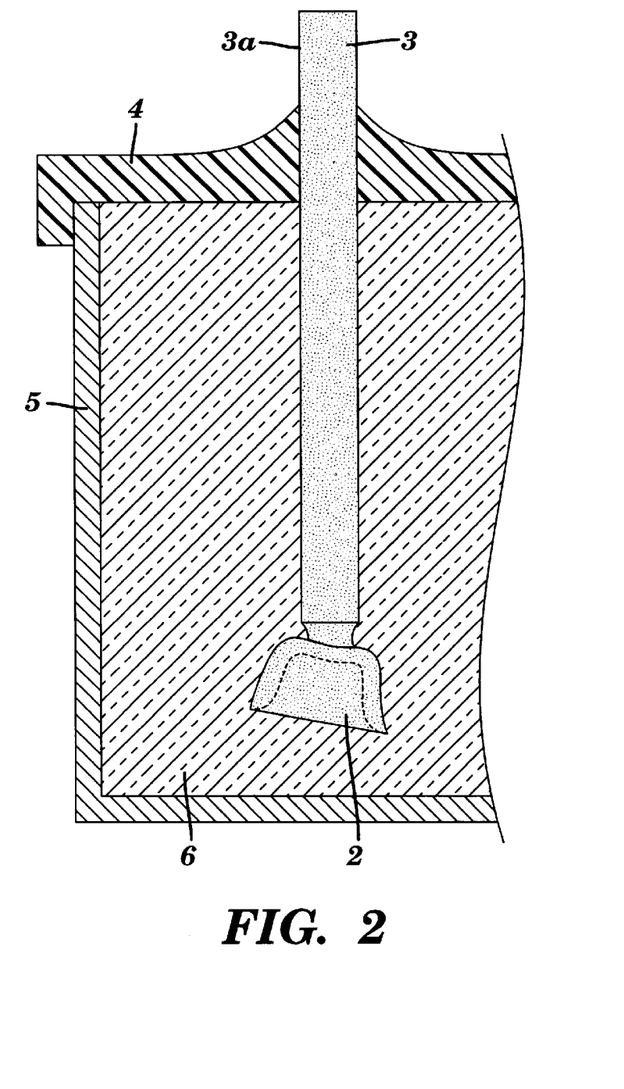
FIG. 2 shows the model after embedding in an investment material.

Initially, a dimensionally and shape accurate model 2 of the dental product, for example, a crown, is modeled from wax on an impression of a tooth stump 1 (FIG. 1). The model wall thickness is approximately 0.5 to 0.8 mm. To the upper part of the model is attached a sprue forming means, such as a ceramic cylinder 3 ($Al_2O_3$), the cylinder being enveloped with a thin, e.g., 0.05 to 0.2 mm, preferably 0.15 mm, thick wax coating 3a. Following the removal of the crown model from working stump 1 fixed to cylinder 3, the latter is fixed in the central hold of, for example, plastic flask cover 4, (FIG. 2). Cylinder 3 and crown model 2 are placed in a metal flask 5, which is sealed at the top by cover 4. A refractory, phosphate-bound quartz cristobalite investment material 6 is now introduced into flask 5 which hardens through a chemical setting process. After hardening the investment material 6, cover 4 with cylinder 3 is removed, whilst the crown model 2 is left in investment material 6. The flask 5 is then heated in a furnace for approximately 2 hours to 1000° C. This leads to the burning out of the wax crown model 2, so that it is replaced in investment material 6 by a mold cavity 7 (FIG. 3), which is open to the outside through the pouring channel 8 formed by the removed cylinder 3.

Figure 3:
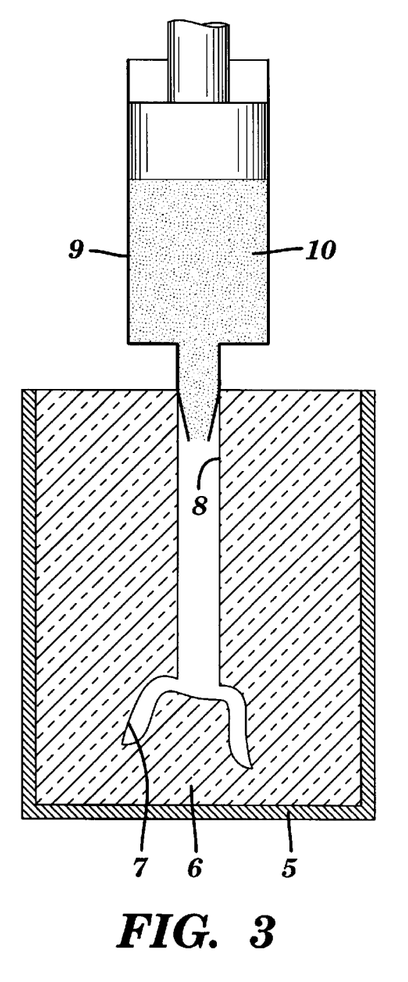
FIG. 3 show the insertion of a material into the filling channel of the investment material.
Figure 4:
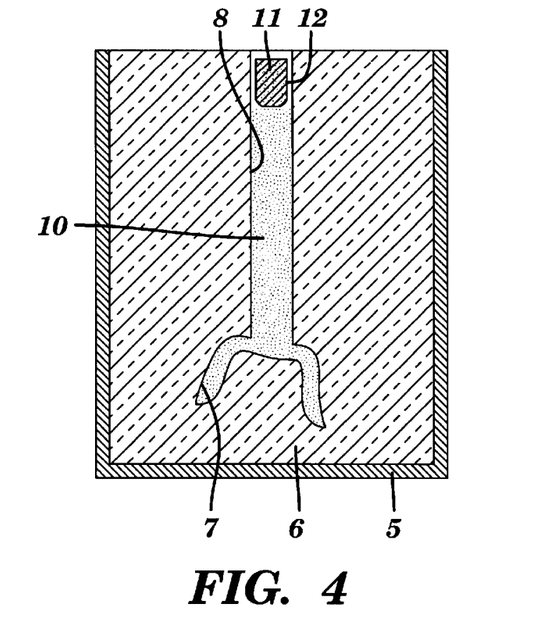
FIG. 4 shows the investment material with filled and closed pouring channel.

Using a suitable filling means 9, the aforementioned glass ceramic material 10 is now introduced by injecting or pressing it into pouring channel 8. Preferably, the glass ceramic is provided in the form of a glass ceramic blank, as described above, which is pressed into pouring channel 8. Alternatively, the glass ceramic material is in the form of a powder or liquid, and is injected. The upper region of the pouring channel is then freed from filling material and at this point there is inserted a ceramic sealing piston 11 into pouring channel 8. The edges of piston 11 resting on the filling material 10 are appropriately chamfered or rounded.

Flask 5 with the introduced filling material 10 is now slowly heated under vacuum to 1180° C. in a furnace and when it reaches 1000° C., the glass ceramic material becomes plastic. The final temperature of 1180° C. is maintained for approximately 20 minutes, which is sufficient to bring about a complete burning out of the organic material.

Figure 5:
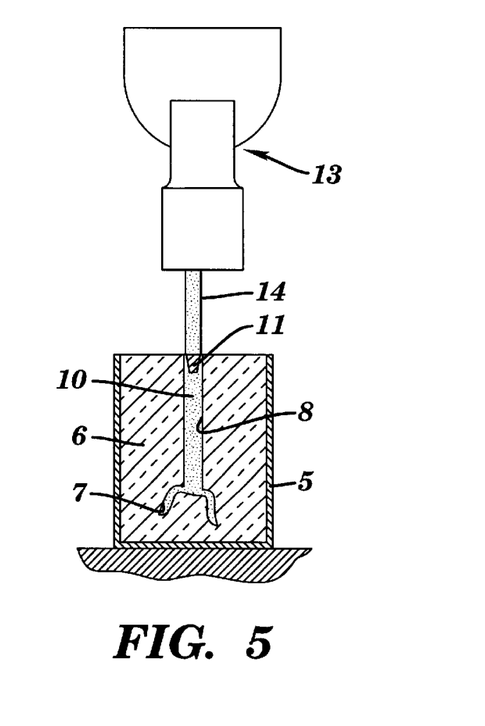
FIG. 5 shows the pressing of the plasticizable material into the mold cavity.

One or more pressing actions are now performed on piston 11 using a pressing means 13 having a ceramic punch or piston 14, so that the plastic filling material is pressed into mold cavity 7. Ceramic punch 14 must obviously have a somewhat smaller cross-section than the pouring channel 8. Pressures of 0.5 to 3 bar, preferably of 0.5 to 1 and particularly 0.8 can be used, dependant the volume of the dental appliance to be produced. If there are several pressure strokes, the first can take place before the final temperature is reached, e.g., at 1060° C., and then a second pressure stroke can take place at 1180° C. following the approximately 20 minutes hold time.

By virtue of the application of pressure to the plastic heated filling material in mold cavity, it is possible to avoid the shrinkage losses which are otherwise unavoidable when firing this material. The molding removed from the mold after cooling corresponds in shape and dimensions to the crown model formed at the start of the process.

If necessary, intermittent pressing can take place outside the furnace provided for achieving the necessary plasticizing and firing temperatures. When possible, however, it is preferred that the pressing processes be performed through a corresponding opening in the furnace top while the flask remains in the furnace of the present invention.

After separating the pouring shoulder from the molding, the latter is cleaned, e.g., by blasting with glass beads and can then be faced in the conventional manner by the coating with dentine and melt coating composition.

Instead of crown caps as described hereinbefore, the process can also be used for producing translucent all porcelain crowns or glass crowns. Modeling and embedding the crown model take place as described hereinbefore. However, when heating and pressing the translucent filling material it is necessary to choose different heating times. The first pressing process can be performed on reaching a temperature of 960° C. and the second process at 1060° C., pressing being maintained for 20 minutes. Heating may take place under the vacuum. Here again the molding can be cleaned after removal from the mold, e.g., by means of glass beads and investment mass adhering in the edge region can be removed in the ultrasonic bath.

After removing the pouring shoulder, the surface of the crown can be provided with a glaze or enamel and then fired again. A variety of different, generally tooth colored compositions are available, which have different translucency, which greatly facilitates surface painting.

In the previously described example the crown model was produced entirely from wax. However, it is also possible to produce the model from a wax/porcelain mixture, e.g. in a ration of 1:7. The filling material is not then introduced into the cavities 7, 8 of the investment material 6 and instead the ceramic material can be inserted in the filling channel 8 in powder form or as a molded ceramic powder blank. However, the heating and pressing processes remain the same as described hereinbefore.

The process can be performed advantageously in a specifically designed furnace. The furnace (FIG. 6) comprises a lower part 22 and an upper part 23, into which is integrated a heating system 24. By means of pressing cylinder 25 is arranged outside the furnace, it is possible to move a piston 26 up and down which acts on piston rod 27 during the pressure operation.

Figure 6:
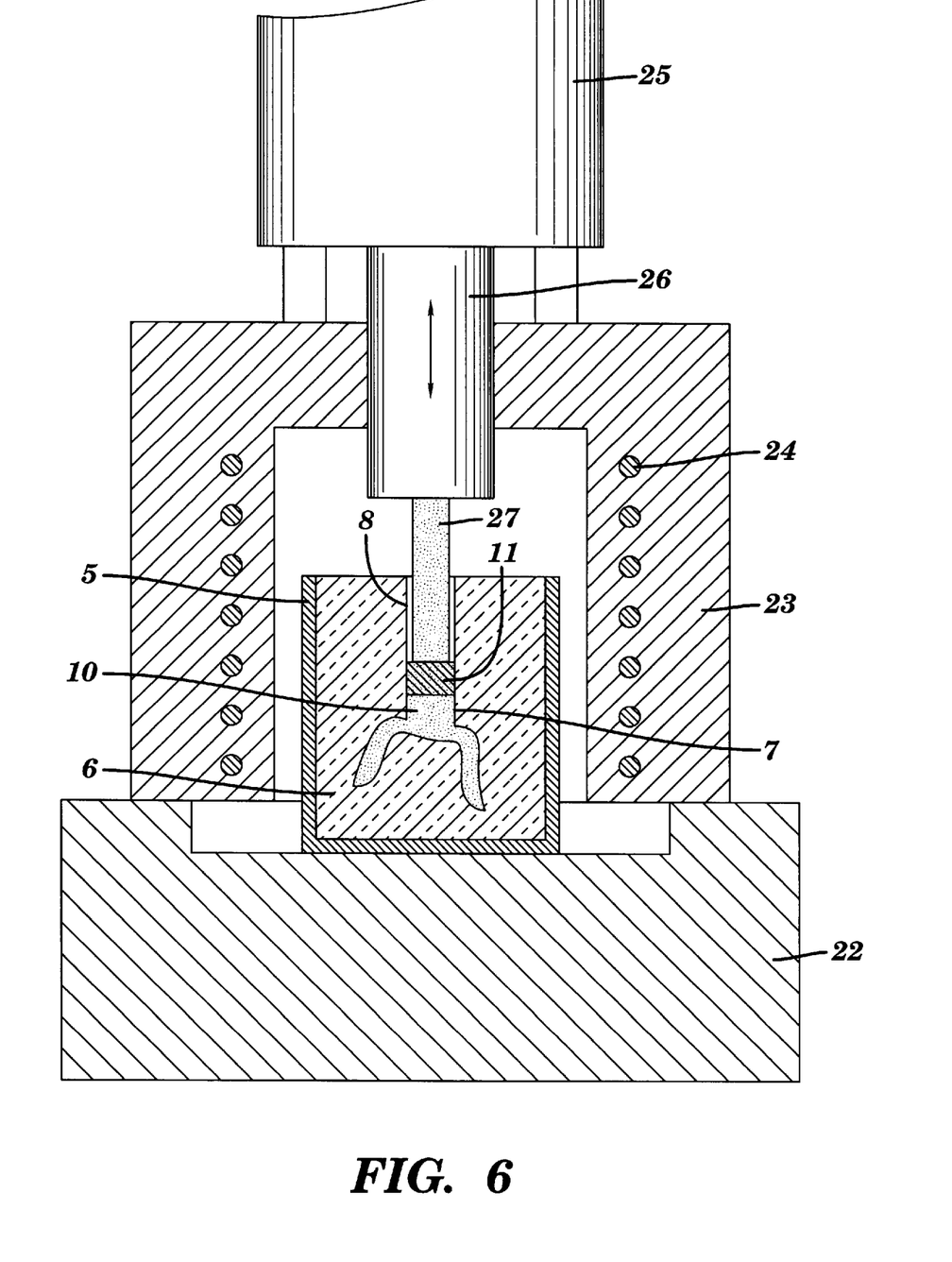
FIG. 6 shows a furnace with inserted flask in cross-section.

Piston rod 27 preferably has a smaller diameter than sealing piston 11, while piston 26 of the pressing cylinder 25 has preferably a larger diameter than the piston rod 27 So that there is no need to precisely center the flask with piston rod 27.

However, it is also possible for the piston rod 27 to simultaneously serve as a sealing piston and then there is no need for a separate sealing piston 11.

In the operating state, the furnace contains flask 5 with the cured investment material 6 in which, as described above, has been formed a mold cavity 7 with pouring channel 8. The latter contains the sealing piston 11, by means of which pressure is exerted on glass ceramic material 10.

During the heating and cooling process, the furnace is controlled electronically in conventional manner. The furnace upper part 23 is swung away on inserting flask 5. Alternatively the separation between the lower part 22 and upper part 23 of the furnace can take place in such a way that the part 23 is moved upwards in elevator-like manner on corresponding guides to provide space for the insertion of flask 5.

Piston 26 is passed in air-tight manner through the upper part 23 of the furnace and the seal between the upper and lower parts is air-tight, so that the interior of the furnace can also be evacuated when necessary. For this purpose, the furnace interior can be connected to a vacuum line.

As described above, pressure can be exerted by pressing means 25 throughout the heating and cooling process, i.e., for as long as the molding material is plasticized. It is also possible to only intermittently pressurize the sealing piston 11 and according to the invention this not only takes place at the start during the filling of the mold cavity, but also during the hardening or cooling of the mass.

It was ascertained that conventional lithium disilicate glass ceramics do not satisfy various requirements for further processing to dental products by plastic deformation. A requirement of this further processing is that the glass ceramic blank in the plastic state should flow in a controlled manner and at the same time react only to a small extent with the investment material. Surprisingly, these two properties are obtained with the glass ceramic according to the present invention by the use of $La_2O_3$ and $Al_2O_3$ in the specified quantities. It is very surprising that the glass ceramic blank is free flowing and can be pressed in the plastic state, although it is already a glass ceramic material. In contrast to this, the prior art exclusively teaches the use of a glass as a liquid melt, since otherwise pressing in the plastic state is not possible because the viscosity is too high.

It has proved to be particularly advantageous if the glass ceramic blank has a viscosity of $10^5$ to $10^6$ Pa.s during plastic deformation in stage (g1).

On the other hand, the glass ceramic blank may also be machined in stage (g2) to a dental product of the desired geometry, for which purpose, in particular, computer-controlled milling machines are used. A conventional technique for the construction of a ceramic dental restoration (i.e., crown or bridge) is as follows: first an impression is taken by the dentist of the area that has been prepared to receive the dental restoration. Thereafter, a refractory die is prepared from the impression. The ceramic powder is then applied to the refractory die using conventional procedures. Once the dental ceramic material is in its predetermined and desired shaped, it is fired as in conventional in the art for the preparation of a fired dental porcelain. Once the ceramic composition has been fired, a dental restoration in the shape of a crown or bridge, for example, is formed.

In many cases it is advantageous that the dental product of the desired geometry obtained after stage (g1) or (g2) is provided with a coating in stage (h). A suitable coating is, in particular. a ceramic, a glass ceramic, a glass, a glaze and/or a composite. Coatings which have a sintering temperature of 650° to 950° C. and a coefficient of linear expansion that is smaller than that of the dental product to be coated are advantageous. Coatings whose coefficients of linear expansion do not differ by more than $\pm 3.0 \times 10^{-6} K.^{-1}$ from those of the substrate are particularly advantageous.

A coating is applied in particular by sintering on the dental product, for example, a glass, a glass ceramic or a composite. During this sintering process, the dental product containing lithium disilicate glass ceramic is, however, brought into a temperature range which is above the transformation point of the residual glass matrix of the glass ceramic. Conventional lithium disilicate glass ceramics are often deformed in an undesirable manner during this process since their dimensional stability on heating is too low. Dimensional stability means that the dental product shows exact fitting to the tooth when used in the dental restoration. The dental product according to the intention, however, has an excellent, dimensional stability on heating up to 900° C., for which in particular this $La_2O_3$ and $Al_2O_3$ content in the specified quantities is responsible.

Apart from sintering on, other processes of the kind that are customary for the manufacture of material composites, e.g. bonding or soldering, may also be used.

Moreover, the glass ceramic according to the invention also has very good chemical stability, which is brought about by the use of $Al_2O_{31}$ $La_2O_{31}$ MgO, and ZnO in the specified quantities.

The dental product according to the present invention can have an acid resistance below 75 $\mu g/cm^2$.

Apart from the above-mentioned properties of the lithium disilicate glass ceramics according to the present invention, they also have the following other important properties, as a result of which they are particularly suitable for use as a dental material or component thereof:

High bending fracture strengths of 200 to 400 MPa. The method of measurement is explained in the Examples.

High fracture toughness values of 3 to 4.5 $MPam^{0.5}$. The method of determination is explained in the Examples.

A translucency comparable with that of the natural tooth, although the production of the glass ceramic according to the invention takes place at least partially by the mechanism of surface crystallization. This is surprising because opacity is often brought about in other glass ceramic systems due to surface crystallization effects or initialization of surface nucleation, as in the case of the formation of surface distortion due to β-quartz mixed crystal formation.

Ability of the color to be matched to that of a natural tooth by using color components. It is surprising that in spite of the color components that can be used, the strength and toughness of the glass ceramic is not adversely impaired. For example, it is known that the crystallization of lucite glass ceramics, which are likewise produced by the mechanism of surface crystallization, is greatly influenced by such additives and that their strength is often very much reduced thereby.

Ease of etching of the glass ceramic if used as dental restoration. For example, a retentive pattern is produced on the inner side of a dental crown according to the invention by controlled etching. When a retentive pattern is produced, no layer-like erosion of the glass ceramic takes place, as is the case, for example, with mica glass ceramics, but small open-pored structures are produced in the surface region. As a result of a retentive pattern of this kind, it becomes possible to fix the glass ceramic to the natural tooth with the aid of an adhesive bonding system.

Suitable shaped dental products according to the invention which contain the glass ceramic according to the invention are, in particular, dental restorations, such as, for example, an inlay, an onlay, a bridge, a post construction, a facing, jackets, veneers, facets, connectors, a crown or a partial crown.

While the present invention is described for use in making dental products, it is understood that the glass ceramic of the invention can be used to form glass ceramic articles, for example, aerospace, automotive, medical device and/or tableware articles wherein the advantageous physical properties of the lithium disilicate glass ceramic are desirable for that particular application. Further, any known forming technique to produce the glass-ceramic of the invention, for example, drawing, floating, pressing, rolling, spinning, etc., can be employed depending on the application of the glass ceramic.

The invention will be explained in more detail below on the basis of examples.

EXAMPLES Examples 1 to 21

A total of 21 different glass ceramics according to the invention and shaped dental products with the chemical composition given in Table I were prepared by carrying out stages (a) to (f) of the process described.

A starting glass with the chemical composition given in Table I, Example 21, was prepared initially. To this end, a batch of oxides, carbonates and phosphates was melted in a platinum/rhodium crucible at a temperature of 1500° to 1600° C. for a homogenization period of one hour. The glass melt was quenched in water, and the glass frit formed was dried and milled to an average particle size of 20 to 30 $\mu$m. Coloring by means of coloring bodies was not necessary due to the use of glass-coloring oxides, namely $CeO_2$, $TiO_2$ and $Fe_2O_3$.

The colored glass powder was then pressed by means of a uniaxial dry press at room temperature and at a pressure of 750 bar to form cylindrical starting glass blanks, hereinafter referred to as green compacts, with a mass of about 4 g. The green compacts were sintered in a furnace under vacuum to produce the glass ceramic according to the invention in the form of a blank. In a first phase, the green compact was fired for one hour at 500° C. The blank was then densely sintered in a second sinter treatment at 850° C. for 2 hours, the rate of heating being 30° C./min.

Properties of the Blanks

Optical Properties

The blanks obtained had optical properties, e.g. translucency, color and opacity comparable with conventional dental ceramic commercial products, such as IPS Empress OI blanks from IVOCLAR AG, Liechtenstein.

Biaxial Strength

To determine the biaxial strength, sintered blanks were sawn into discs with a diameter of 12 mm and a thickness of 1.1 mm. The biaxial strength was determined with three-point bearing test apparatus (steel balls with a diameter of 3.2 mm) with a force being introduced at one point by means of a punch with a diameter of 1.6 mm according to ISO 6872-1995 E "Dental Ceramic". The rate at which the load

TABLE I

| Exp. No. | $SiO_2$ | $Al_2O_3$ | $P_2O_5$ | $K_2O$ | $Na_2O$ | $Li_2O$ | $B_2O_3$ | $TiO_2$ | $ZrO_2$ | $CeO_2$ | F | $La_2O_3$ | ZnO | MgO | $Fe_2O_3$ |
|---|---|---|---|---|---|---|---|---|---|---|---|---|---|---|---|
| 1 | 65.0 | 4.8 | 3.7 | 4.0 | — | 14.2 | — | — | — | — | — | 0.1 | 4.6 | 3.6 | — |
| 2 | 66.9 | 1.1 | 3.8 | 3.4 | — | 14.8 | — | — | — | — | — | 1.8 | 7.9 | 0.3 | — |
| 3 | 66.6 | 1.0 | 3.4 | 3.7 | — | 15.1 | — | — | — | 0.6 | — | 6.0 | 3.5 | 0.1 | — |
| 4 | 66.2 | 0.7 | 2.5 | 13.4 | — | 14.7 | — | — | 0.85 | 0.6 | — | 0.2 | 0.7 | 0.15 | — |
| 5 | 73.1 | — | — | 4.3 | — | 15.8 | — | — | — | — | — | 1.0 | 5.5 | 0.3 | — |
| 6 | 65.0 | 4.7 | 3.6 | 4.0 | — | 14.3 | — | — | — | — | — | 0.3 | 3.3 | 4.8 | — |
| 7 | 75.3 | 1.0 | 3.7 | 4.1 | — | 11.0 | — | — | — | — | — | 0.6 | 4.3 | — | — |
| 8 | 79.8 | 0.5 | 2.1 | 2.0 | — | 12.1 | — | — | — | — | — | 1.5 | 1.8 | 0.2 | — |
| 9 | 70.1 | 0.7 | 2.5 | 2.8 | — | 18.9 | — | — | — | — | — | 1.7 | 3.0 | 0.3 | — |
| 10 | 69.5 | 1.1 | 3.8 | 4.3 | — | 15.4 | — | — | — | 0.55 | — | 0.3 | 4.9 | 0.15 | — |
| 11 | 68.4 | 1.1 | 3.7 | 4.2 | — | 15.1 | 1.7 | — | — | — | — | 0.8 | 4.8 | 0.2 | — |
| 12 | 69.8 | 1.0 | 3.8 | 4.3 | — | 15.5 | 0.25 | 0.3 | — | 0.4 | 0.15 | 0.2 | 4.1 | 0.2 | — |
| 13 | 70.5 | 0.9 | 3.2 | 4.0 | — | 15.7 | — | — | — | 0.5 | 1.25 | 0.4 | 3.4 | 0.15 | — |
| 14 | 57.2 | 2.8 | 10.8 | 3.7 | 2.1 | 14.5 | — | — | 3.2 | — | 0.5 | 0.3 | 4.9 | — | — |
| 15 | 71.4 | 1.1 | 4.0 | 4.4 | — | 15.9 | — | — | — | — | — | 0.5 | — | 2.7 | — |
| 16 | 71.1 | 1.1 | 3.9 | — | 2.9 | 15.7 | — | — | — | — | — | 0.2 | 5.1 | — | — |
| 17 | 64.3 | 1.0 | 3.8 | 4.2 | 2.3 | 15.2 | — | — | 3.4 | — | 0.5 | 1.0 | 4.3 | — | — |
| 18 | 69.3 | 1.0 | 3.8 | 3.8 | — | 15.3 | — | 1.5 | — | 1.6 | — | 0.8 | 2.7 | 0.2 | — |
| 19 | 72.6 | — | — | 4.1 | — | 16.1 | — | 0.9 | — | 0.5 | — | 3.2 | 2.2 | 0.4 | — |
| 20 | 71.5 | 1.1 | 4.0 | 3.9 | — | 16.6 | 0.4 | — | 0.8 | 0.3 | 0.25 | 1.0 | 0.15 | — | — |
| 21 | 69.6 | 1.1 | 3.9 | 3.3 | — | 15.4 | — | 0.5 | — | 0.3 | 0 | 0.3 | 5.2 | 0.2 | 0.2 |

Example 22

This Example describes the preparation of a glass ceramic according to the invention and the potential use thereof as a framework material for the preparation of a fully ceramic product which can be formed individually, such as a crown or a multiple-unit bridge, on which in addition a matching dental sintered ceramic is fired on.

was applied was 0.5 mm/min. The biaxial strength determined under these conditions was 261±31 MPa.

The glass ceramic blanks obtained were finally pressed under vacuum in the viscous state using the pressing method and pressing furnace according to EP-A-0 231 773 to obtain the sample geometry required for the test in question. The standby temperature of the pressing furnace was 700° C., and the rate of heating to the pressing temperature was 60° C./min; the pressing temperature was 920° C., the retention time at the pressing temperature was 10 min and the pressure was 5 bar. After the pressing process, the die was air cooled and the specimens were removed from the die by sandblasting with $Al_2O_3$ powder and glass beads.

The specimens obtained had the following properties:

Properties of Glass Ceramics Subjected to Plastic Deformation

Optical Properties

The glass ceramic having undergone plastic deformation had translucence properties which enable the dental technician to prepare fully ceramic dental products from it, e.g. crowns of multiple-unit bridges which meet the optical requirements of a natural tooth. Due to the use of glass-coloring oxides in the basic glass, the hot-pressed glass ceramic was tooth-colored. The color intensity could be adjusted by controlling the concentration of the coloring oxides or by the additional use of the coloring bodies.

The combination of translucent framework material and translucent to transparent dental sintered glass ceramic with a coefficient of expansion of 9.1 μm/mK, which was sintered in layers at 800° C. under vacuum onto the crown of bridge structure having undergone plastic deformation led to translucent, fully ceramic dental restorations which meet the stringent aesthetic requirements for such products.

3-point Bending Strength

Bars with the dimensions 1.5×4.8×20 mm³ were pressed and these were ground on all sides with SiC wet-grinding paper (grain size 1000). The bending strength was determined with a test specimen span of 15 mm and a load applied at a rate of 0.5 mm/min. according to ISO 6872-1995 E "Dental ceramic". The 3-point bending strength determined under these conditions was 341±98 MPa.

Coefficient of Linear Thermal Expansion

Cylindrical specimens with a diameter of 6 mm and a length of 20 mm were pressed. The coefficient of expansion determined for these specimens in the temperature range from 100° to 500° C. was 10.6 μm/mK.

Fracture toughness $K_{1c}$

Bars with the dimensions 1.5×4.8×20 mm³ were pressed and these were ground on all sides with SiC wet-grinding paper (grain size 1000). Using a diamond wheel (0.1 mm thick), the specimens were notched on one side to a depth of 2.8 mm and then tested for their 3-point bending strength. The bending strength was determined with a test specimen span of 15 mm and a loan applied at rate of 0.5 mm/min. The $K_{1c}$ value determined was 4.0±0.2 MPa m$^{05}$.

Acid Resistance

Disc-shaped specimens with a diameter of 15 mm and a thickness of 1.5 mm were pressed and then ground on all sides with SiC wet-grinding paper (grain size 1000). The loss of mass per unit area of these specimens determined according to ISO 6872-1995 E "Dental ceramic" was determined after 16 hours' storage in 4 vol. % aqueous acetic acid solution, and it was only 73 μg/cm² and was thus markedly below the required standard value for dental ceramic materials of 2000 μg/cm².

Example 23

This Example describes the preparation of a glass ceramic according to the invention and the potential use thereof as a framework material for the preparation of a fully ceramic product which can be formed individually, such as a crown or a multiple-unit bridge, onto which in addition a matching dental sintered ceramic has been fired on.

A starting glass with the chemical composition given in Table I, Example 18, was prepared initially. To this end, a batch of oxides, carbonates and phosphates was melted in a platinum/rhodium crucible at a temperature of 1500° to 1600° C. for a homogenization period of one hour. The glass melt was quenched in water and the glass frit formed was dried and milled to an average particle size of 20 to 30 μm. Commercial coloring bodies and fluorescing agents were added to the glass powder and homogenized.

The colored glass powder was then pressed by means of a uniaxial dry press at room temperature and at a pressure of 750 bar to form cylindrical green compacts with a mass of about 4 g. The green compacts were sintered in a furnace under vacuum to obtain the glass ceramic according to the invention in the form of a blank. In a first phase the green compact was fired at 500° C. for 20 minutes. The blank was then densely sintered for 30 minutes at 850° C. in a second sinter treatment, the rate of heating being 30° C./min. Unless otherwise specified, the procedures used to determine the properties of the glass ceramic blank are the same as those given in Example 22.

Properties of the Blanks

Optical Properties

The blanks obtained had optical properties such as translucency, color and opacity comparable with conventional dental ceramic commercial products, e.g. IPS Empress Dentin 24 blanks from IVOCLAR AG, Liechtenstein.

Biaxial Strength

The biaxial strength was 270±38 MPa.

The glass ceramic blanks obtained were finally pressed under vacuum in the viscous state to the desired specimen geometry for the test in question using the pressing process and pressing furnace according to EP-A-O 231 773. The standby temperature of the pressing furnace was 700° C., the rate of heating to the pressing temperature was 60° C./min, the pressing temperature was 920° C., the retention time at the pressing temperature was min. and the pressure was 5 bar. After the pressing process, the die was air-cooled and the specimens were removed from the die by sand blasting with $Al_2O_3$ powder and glass beads.

The properties of the specimens obtained were determined according to the procedure described in each case in Example 22.

Properties of Glass Ceramic Subjected to Plastic Deformation

Optical Properties

The glass ceramic having undergone plastic deformation had translucence properties which enable the dental technician to prepare fully ceramic dental products from it, e.g. crowns of multiple-unit bridges, which comply with the optical requirements of a natural tooth. The combination of translucent framework material and translucent to transparent dental sintered glass ceramic with a coefficient of expansion of 9.1 μm/mK which was sintered in layers at 800° C. under vacuum onto the crown or bridge structure which had undergone plastic deformation led to translucent, fully ceramic dental restorations which meet the stringent aesthetic requirements of such dental products.

3-point Bending Strength

The 3-point bending strength was 347±37 MPa.

Coefficient of Linear Thermal Expansion

The coefficient of expansion determined in the temperature range from 100 to 500° C. was 10.7 μm/mK.

Fracture Toughness $K_{1c}$

The $K_{1c}$ value determined was 3.8+0.5 MPa m$^{0.5}$.

Acid Resistance

The loss of mass per unit area determined according to ISO 6872-1995 after 16 hours' storage in 4 vol. % aqueous acetic acid solution was markedly below the standard value for dental ceramic materials of 2000 μg/cm$^2$.

What is claimed:

1. A dental product comprising a lithium disilicate glass ceramic comprising the following components:

| Component | Wt. % |
|---|---|
| SiO$_2$ | 57.0 to 80.0 |
| Al$_2$O$_3$ | 0 to 5.0 |
| La$_2$O$_3$ | 0.1 to 6.0 |
| MgO | 0 to 5.0 |
| ZnO | 0 to 8.0 |
| K$_2$O | 0 to 13.5 |
| Li$_2$O | 11.0 to 19.0 |
| P$_2$O$_5$ | 0 to 11.0 |
| Color components | 0 to 8.0 |
| Additional components | 0 to 6.0 | wherein
Al$_2$O$_3$ + La$_2$O$_3$ equals 0.1 to 7.0 wt. % and
MgO + ZnO equals 0.1 to 9.0 wt. %.

2. The dental product according to claim 1, wherein the dental product is translucent.

3. The dental product according to claim 1, wherein the dental product has the color of a natural tooth.

4. The dental product according to claim 1, wherein the dental product has a bending strength of 200 to 400 MPa.

5. The dental product according to claim 1, wherein the dental product has an acid resistance below 75 μg/cm$^2$.

6. The dental product according to claim 1, wherein the dental product has fracture toughness value of 3 to 4.5 MPam$^{0.5}$.

7. The dental product according to claim 1, further comprising a coating.

8. The dental product according to claim 7, wherein the coating is a ceramic, a class ceramic, a glass, a glaze, or a composite.

9. The dental product according to claim 1, wherein the dental product has a dimensional stability at up to 900° C.

10. The dental product according to claim 1, which is an inlay, an onlay, a bridge, a post construction, a veneer, a crown, or a partial crown.

* * * * *